United States Patent
Brandenburg et al.

(10) Patent No.: US 6,747,154 B2
(45) Date of Patent: Jun. 8, 2004

(54) PROCESS FOR PREPARING SCOPINE ESTERS

(75) Inventors: Joerg Brandenburg, Wiesbaden (DE); Waldemar Franz-Augustin Pfrengle, Biberach (DE); Werner Rall, Mittelbiberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/339,480

(22) Filed: Jan. 9, 2003

(65) Prior Publication Data

US 2003/0232993 A1 Dec. 18, 2003

Related U.S. Application Data

(60) Provisional application No. 60/351,680, filed on Jan. 25, 2002.

(30) Foreign Application Priority Data

Jan. 12, 2002 (DE) .......................... 102 00 943

(51) Int. Cl.$^7$ ............................. C07D 451/10
(52) U.S. Cl. .................. 546/91; 549/59; 549/60; 549/473; 560/100; 560/101; 562/468
(58) Field of Search .................. 546/91; 549/59, 549/60, 473; 560/100, 101; 562/468

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,952,505 A | 9/1999 | Banholzer et al. | |
| 6,486,321 B2 | 11/2002 | Banholzer et al. | |
| 6,506,900 B1 | 1/2003 | Banholzer et al. | |

FOREIGN PATENT DOCUMENTS

| | | |
|---|---|---|
| DE | 100 50 994 A1 | 4/2002 |
| DE | 100 50 995 A1 | 4/2002 |
| DE | 100 64 816 A1 | 6/2002 |
| EP | 0 418 716 A1 | 3/1991 |
| WO | WO 92/16528 A1 | 10/1992 |

OTHER PUBLICATIONS

Windholz, M. et al; "The Merck Index, tenth edition", Merck & Co., Inc., (1983), No. 7824, p. 1142; XP002239794.

Heidemann, D. R.; "High–pressure liquid chromatographic determination of methscopolamine nitrate, phenylpropanolamine hydrochloride, pyrilamine maleate, and pheniramine maleate in tablets,"; J. Pharm. Sci., Bd. 70, Nr. 7, 1981, pp. 820–822; Chemical Abstracts, vol. 95, No. 14, XP002239795.

(List continued on next page.)

Primary Examiner—Evelyn Mei Huang
(74) Attorney, Agent, or Firm—Robert P. Raymond; Timothy X. Witkowski; Anthony P. Bottino

(57) ABSTRACT

A process for preparing a compound of formula 1

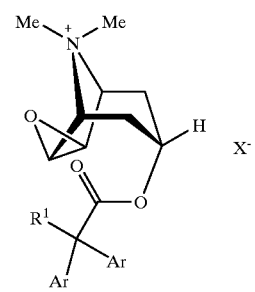

from a compound of formula 2

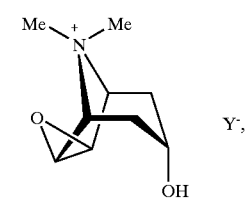

the process comprising reacting in one step the compound of formula 2 with a compound of formula 3

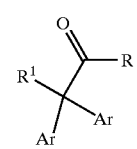

wherein:
  X$^-$ is chlorine, bromine, iodine, methanesulfonate, or trifluoromethanesulfonate;
  R$^1$ is hydroxy, C$_1$–C$_4$-alkyl, C$_1$–C$_4$-alkoxy, CF$_3$, or fluorine;
  Ar is phenyl, naphthyl, thienyl, and furyl, each optionally mono- or disubstituted with one or two groups selected from C$_1$–C$_4$-alkyl, C$_1$–C$_4$-alkoxy, hydroxy, fluorine, chlorine, bromine, or CF$_3$;
  Y$^-$ is chlorine, bromine, iodine, methanesulfonate, or trifluoromethanesulfonate; and
  R is hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl, or —S-phenyl.

25 Claims, No Drawings

OTHER PUBLICATIONS

Banholzer, R. et al; "Process For Preparing An Anticholinergic", US Pub. No. 2002/0133010 A1; Sep. 19, 2002.

Meissner, H. et al; "Anticholinergics, Processes For Preparing Them, And Pharmaceutical Compositions Containing Them"; US Pub. No. 2002/0119991 A1; Aug. 29, 2002.

Meissner, H. et al; "Anticholinergics Which May Be Used As Medicaments As Well As Processes For Preparing Them"; US Pub. No. 2002/0115680 A1; Aug. 22, 2002.

Chemical Abstract: CA 136:325718 for DE 100 05 995 A.

Chemical Abstract: CA 136:310064 for DE 100 50 995 A.

Chemical Abstract: CA 137:47348 for DE 100 64 816 A.

Chemical Abstract: CA 116:20937 for EP 0 418 716 A.

PROCESS FOR PREPARING SCOPINE ESTERS

RELATED APPLICATION

Benefit under 35 U.S.C. § 119(e) of prior U.S. provisional application Serial No. 60/351,680, filed Jan. 25, 2002, is hereby claimed; and U.S. provisional application Serial No. 60/351,680 is hereby incorporated by reference in its entirety.

FIELD OF THE INVENTION

The invention relates to a new process for preparing scopine esters of general formula 1

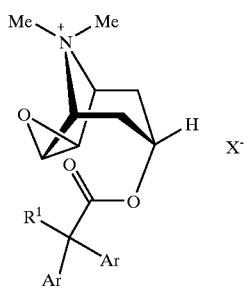

wherein $X^-$ and the groups $R^1$ and Ar may have the meanings given in the claims and in the specification.

BACKGROUND OF THE INVENTION

Anticholinergics may appropriately be used to treat a number of diseases. Particular mention should be made, for example, of the treatment of asthma or chronic obstructive pulmonary disease (COPD). For treating these diseases, WO 92/16528 proposes, for example, anticholinergics which have a scopine, tropenol, or tropine basic structure.

The problem on which WO 92/16528 is based is the preparation of anticholinergically active compounds which are characterized by their long-lasting activity. To solve this problem, WO 92/16528 discloses inter alia benzilic acid esters of scopine, tropenol, or tropine.

For treating chronic diseases, it is often desirable to prepare pharmaceutical compositions with a longer-lasting effect. This will generally ensure that the concentration of the active substance needed to achieve the therapeutic effect is present in the body for a longer period of time without the need for the pharmaceutical composition to be administered repeatedly and all too frequently. Moreover, if an active substance is administered at longer intervals of time, this contributes to the feeling of well-being of the patient to a considerable degree. It is particularly desirable to provide a pharmaceutical composition which can be used to therapeutically good effect by administering it once a day (single dose). A single application per day has the advantage that the patient can become accustomed relatively quickly to the regular taking of the medicament at a particular time of the day.

If it is to be used as a medicament for administration once a day, the active substance which is to be given must meet particular requirements. First of all, the desired onset of the activity after the administration of the pharmaceutical composition should occur relatively quickly and ideally the activity should remain as constant as possible over a fairly lengthy ensuing period. On the other hand, the duration of activity of the pharmaceutical composition should not greatly exceed a period of about one day. Ideally, an active substance should have an activity profile such that the preparation of a pharmaceutical composition which is intended to be administered once a day and contains the active substance in therapeutically appropriate doses can be properly controlled.

It has been found that the esters of scopine, tropenol, or tropine disclosed in WO 92/16528 do not meet these more stringent requirements. Because of their extremely long duration of activity, significantly exceeding the period of about one day specified above, they cannot be used therapeutically in a single once-a-day dose.

In contrast to the compounds disclosed in WO 92/16528, for example, it is possible to prepare anticholinergically active pharmaceutical compositions which can be administered once a day if scopine esters of formula 1

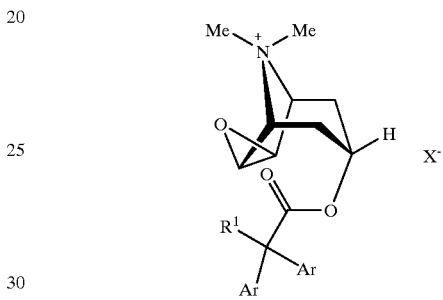

wherein $X^-$ and the groups $R^1$ and Ar may have the meanings specified hereinafter.

In addition to the methods of synthesis disclosed in WO 92/16528 for preparing scopine esters, processes for preparing esters of scopine are also disclosed in EP 418 716 A1, for example. These processes known in the art may also be used to prepare the compounds of formula 1. However, these methods of synthesis are in some cases more complex procedures involving a number of synthesis steps.

The aim of the present invention is to provide a method of synthesis which allows the compounds of general formula 1 to be synthesized more easily.

DETAILED DESCRIPTION OF THE INVENTION

Surprisingly, it has been found that compounds of formula 1

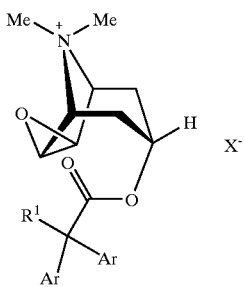

wherein $X^-$ and the groups $R^1$ and Ar may have the meanings specified hereinafter, may be obtained in a single reaction step if compounds of formula 2

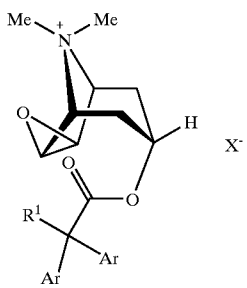

are used as starting material.

Accordingly, the present invention relates to a process for preparing compounds of formula 1

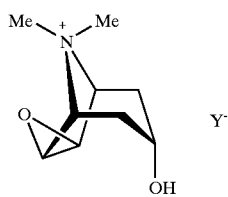

wherein:

X⁻ may represent chlorine, bromine, iodine, methanesulfonate, or trifluoromethanesulfonate;

$R^1$ may represent hydroxy, $C_1$–$C_4$-alkyl, $C_1$–$C_4$-alkoxy, $CF_3$, or fluorine;

Ar may represent a group selected from among phenyl, naphthyl, thienyl, and furyl, which may optionally be mono- or disubstituted by one or two groups selected from among $C_1$–$C_4$-alkyl, $C_1$–$C_4$-alkoxy, hydroxy, fluorine, chlorine, bromine, or $CF_3$, characterized in that a compound of formula 2

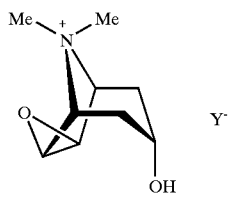

wherein:

Y⁻ may denote chlorine, bromine, iodine, methanesulfonate, or trifluoromethanesulfonate is reacted in one step with a compound of formula 3

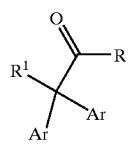

wherein:

R denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl, and —S-phenyl; and the groups $R^1$ and Ar may have one of the above meanings.

Preferably, the present invention relates to a process for preparing compounds of formula 1

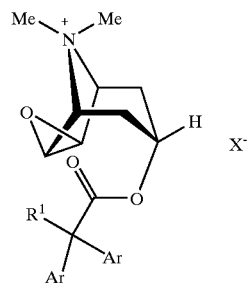

wherein:

X⁻ may represent bromine, methanesulfonate, or trifluoromethanesulfonate;

$R^1$ may represent hydroxy, methyl, $CF_3$, or fluorine;

Ar may represent a group selected from among phenyl, thienyl, and furyl, characterized in that a compound of formula 2

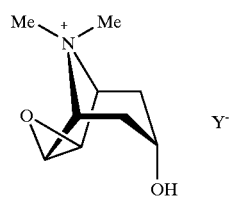

wherein:

Y⁻ may denote bromine, methanesulfonate, or trifluoromethanesulfonate is reacted in one step with a compound of formula 3

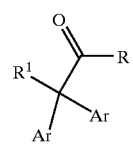

wherein:

R denotes a group selected from among hydroxy, O—N-succinimide, O—N-phthalimide, vinyloxy, and 2-allyloxy; and the groups $R^1$ and Ar may have one of the above meanings.

More preferably, the present invention relates to a process for preparing compounds of formula 1

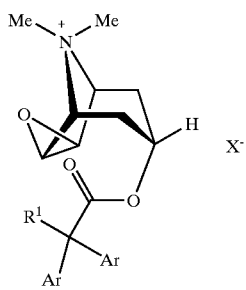

wherein:
X⁻ may represent bromine, methanesulfonate, or trifluoromethanesulfonate;
R¹ may represent hydroxy or methyl; and
Ar may represent phenyl or thienyl,
characterized in that a compound of formula 2

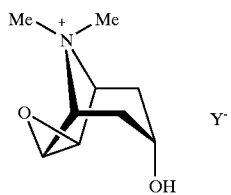

wherein:
Y⁻ may represent bromine, methanesulfonate, or trifluoromethanesulfonate, is reacted in one step with a compound of formula 3

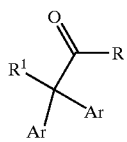

wherein:
R denotes a group selected from among hydroxy, O—N-succinimide, O—N-phthalimide, vinyloxy, and 2-allyloxy, preferably vinyloxy and 2-allyloxy; and
the groups R¹ and Ar may have one of the above meanings.

To perform the process according to the invention the following procedure may be used.

In a first step the compound of formula 3 is taken up in a suitable organic solvent, preferably in a polar organic solvent, most preferably in a solvent selected from among acetonitrile, nitromethane, formamide, dimethylformamide, N-methylpyrrolidinone, dimethylsulfoxide, and dimethylacetamide, while of the abovementioned solvents dimethylformamide, N-methylpyrrolidinone, and dimethylacetamide are particularly preferred. Of particular importance according to the invention are dimethylformamide and N-methylpyrrolidinone, the latter being particularly preferred.

Preferably, between 0.5 L and 2 L, most preferably between 0.75 L and 1.5 L of the abovementioned solvent are used per mol of the compound of formula 3 used.

Depending on the choice of the compound of formula 3, it may be useful in some cases to activate it before the reaction with the compound of formula 2. If derivatives wherein R denotes H are used as the compound of formula 3, it is preferable according to the invention to use, for example, corresponding activating reagents such as carbonyldiimidazole, carbonyldi-1,2,4-triazole, dicyclohexylcarbodiimide, or ethyldimethylaminopropylcarbodiimide, while in this context the use of carbonyldiimidazole is particularly preferred. Between 1 mol and 2 mol of the coupling reagent are used per mol of the compound 3 used wherein R is hydroxy. Preferably, 1 mol to 1.5 mol of the coupling reagent are used. If the abovementioned coupling reagents are used, as is preferred when R is hydroxy, the reaction mixture then obtained is preferably stirred for a period of 1 to 8 hours, preferably 3 to 7 hours, at a temperature in the range from 15° C. to 35° C., preferably at 20° C. to 25° C., before further reaction as described hereinafter.

The reaction mixture of 3 in the abovementioned solvent, optionally after the addition of one of the abovementioned coupling reagents in the case where R is hydroxy, is then adjusted to a temperature below 30° C., preferably to a temperature between −20° C. and 20° C., most preferably to a temperature between −10° C. and 5° C., and the compound of formula 2 is added thereto. Based on the compound 3 originally used, stoichiometric amounts of the compound of formula 2 may be added. However, it is preferable according to the invention for 3 to be present in excess in relation to 2. According to the invention, between 0.5 mol and 1 mol, preferably between 0.7 mol and 0.95 mol, most preferably between 0.75 mol and 0.9 mol of 2 are used per mol of the compound 3 used.

The reaction mixture mentioned above is then combined with a suitable base dissolved in one of the abovementioned solvents. Organic or inorganic bases may be used. Preferably, alkali metal imidazolides are used as the organic bases, which may be generated in situ from the alkali metals and imidazole or the alkali metal hydrides and imidazole, for example. Preferred alkali metal imidazolides include imidazolides of lithium, sodium, or potassium, while sodium or lithium imidazolide are preferred according to the invention. Most preferably, lithium imidazolide is used. Preferred inorganic bases are hydrides of lithium, sodium, or potassium. Most preferably, sodium hydride is used as the inorganic base. Of all the abovementioned bases, lithium imidazolide is most preferably used.

If the intention is to prepare compounds of formula 1 wherein R¹ denotes hydroxy, instead of the abovementioned base-catalyzed reaction, transesterification under milder reaction conditions may also appear advantageous. Zeolites may advantageously be used as catalysts.

If the reaction is carried out with one of the abovementioned bases, at least stoichiometric quantities of base are used per mol of compound 2 used. Preferably, 1 mol to 1.5 mol, preferably 1.1 mol to 1.3 mol of base are used per mol of compound 2 used. If the base is added in the form of a solution, as is the case particularly with the base lithium imidazolide preferred according to the invention which is generated in situ beforehand, it is preferable to use for this purpose the solvent which is already being used to carry out the steps mentioned above. Preferably between 0.3 L and 1.3 L, most preferably between 0.5 L and 1 L of the abovementioned solvent are used per mol of the base used. Once all the base has been added, the mixture is stirred for a period of 4 to 48 hours, preferably 8 to 36 hours, in a temperature range from 15° C.–35° C., preferably at 20° C.–25° C.

An acid H—X is added to the resulting suspension at constant temperature. The choice of acid depends on the anion X⁻ in the desired end product of general formula 1. Insofar as compounds of general formula 1 wherein X⁻ denotes bromide are preferably synthesized within the scope of the present invention, the following procedure is described for the preparation of the bromide-containing end products of formula 1 which are preferred according to the invention. It will be apparent to the skilled man that by a suitable choice of the reagent H—X a corresponding procedure can also be used analogously to prepare compounds wherein X⁻ does not denote bromide.

In order to prepare compounds of formula 1 wherein X⁻ is bromide, preferably 2 mol to 4 mol, more preferably 2 mol to 3 mol, most preferably 2.2 mol to 2.6 mol of hydrogen bromide, based on the compound of formula 3 used, are added at constant temperature. The hydrogen bromide used may be added either in gaseous form or in the form of preferably saturated solutions. Preferably, according to the invention, the hydrogen bromide is added after being dissolved in glacial acetic acid. Most preferably, a 33% hydrogen bromide solution in glacial acetic acid is used. After the addition has ended, the mixture is stirred at constant temperature, possibly also while cooling with ice (between 0.5 and 6 hours).

Finally, the solution obtained is combined with a non-polar organic solvent, preferably with a solvent selected from among acetone, toluene, n-butyl acetate, dichloromethane, diethyl ether, tetrahydrofuran, and dioxane, most preferably toluene or acetone.

After thorough mixing, the product that crystallizes out is separated off and washed with the non-polar solvent mentioned above. In order to remove any water-soluble impurities, the crude product may be treated with aqueous bromide solutions, e.g., sodium or potassium bromide solution.

Further purification of the compounds of formula 1 thus obtained may, if necessary, be carried out by chromatography over silica gel or by recrystallization from suitable solvents such as, e.g., lower alcohols, for example isopropanol.

By using the compounds of formula 2, which are known in the prior art, as starting materials for synthesizing the structures of formula 1, these anticholinergically active structures may be obtained in only one reaction step.

Accordingly, in another aspect, the present invention relates to the use of compounds of formula 2

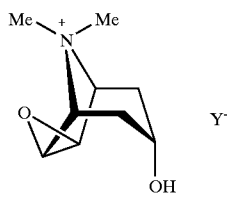

wherein:

Y⁻ denotes chlorine, bromine, iodine, methanesulfonate, or trifluoromethanesulfonate, as starting materials for preparing compounds of formula 1

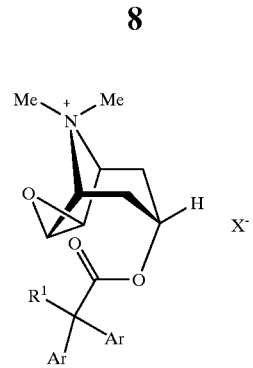

wherein:

X⁻ may represent chlorine, bromine, iodine, methanesulfonate, or trifluoromethanesulfonate;

$R^1$ may represent hydroxy, $C_1$–$C_4$-alkyl, $C_1$–$C_4$-alkoxy, $CF_3$, or fluorine;

Ar may represent a group selected from among phenyl, naphthyl, thienyl, and furyl, which may optionally be mono- or disubstituted by one or two groups selected from among $C_1$–$C_4$-alkyl, $C_1$–$C_4$-alkoxy, hydroxy, fluorine, chlorine, bromine, or $CF_3$.

Preferably, the present invention relates to the use of compounds of formula 2

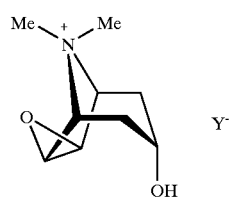

wherein:

Y⁻ denotes bromine, methanesulfonate or trifluoromethanesulfonate, as starting materials for preparing compounds of formula 1

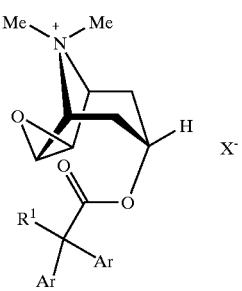

wherein:

X⁻ may represent bromine, methanesulfonate, or trifluoromethanesulfonate;

$R^1$ may represent hydroxy, methyl, $CF_3$, or fluorine;

Ar may represent a group selected from among phenyl, thienyl, and furyl.

Most preferably, the present invention relates to the use of compounds of formula 2

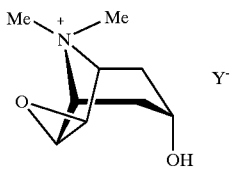

2 wherein:
Y⁻ denotes bromine, methanesulfonate, or trifluoromethanesulfonate, as starting materials for preparing compounds of formula 1

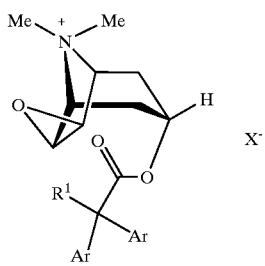

1 wherein:
X⁻ may represent bromine, methanesulfonate, or trifluoromethanesulfonate;
R¹ may represent hydroxy or methyl; and
Ar may represent phenyl or thienyl.

The Examples that follow serve to illustrate some methods of synthesis carried out by way of example. They are intended solely as examples of possible procedures without restricting the invention to their content.

EXAMPLE 1
2,2-Diphenylpropionic acid scopine ester-methobromide

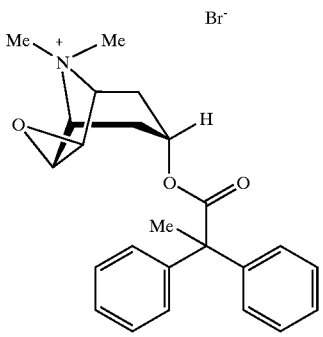

Carbonyldiimidazole (1206 g, 7.44 mol) is added batchwise to a solution of 2,2-diphenylpropionic acid (1629 g, 7.2 mol) in N-methylpyrrolidinone (9 L) and then stirred for 5 hours at ambient temperature (about 23° C.). The reaction mixture is cooled to −3° C. Scopine methobromide (1501 g, 6.0 mol) is added to the reaction mixture. Then a solution of lithium imidazolide (prepared from lithium hydride (59.6 g, 7.12 mol) as well as imidazole (490.2 g, 7.2 mol) in 5 L of N-methylpyrrolidinone is added dropwise. It is stirred for 17 hours at ambient temperature. Hydrogen bromide solution (33% in glacial acetic acid; 2460 mL, 14.25 mol) is added to the resulting suspension at 18° C. to 28° C. with cooling. The suspension is stirred in the ice bath and then combined with toluene (14 L). It is filtered and the filter cake obtained is suspended twice with 5500 mL of 30% potassium bromide solution and suction filtered. The substance thus obtained is dried in the drying cupboard at 40° C. Yield: 2359.3 g (85.8% of theory). To purify it, the crude product (2100 g) is recrystallized from 35.7 L of isopropanol. Yield: 1562.2 g; colorless flakes.

The following may be obtained analogously in a single synthesis step:

EXAMPLE 2
(1α,2β,4β,5α,7β)-7-[(hydroxydi-2-thienylacetyl)oxy]-9,9-dimethyl-3-oxa-9-azoniatricyclo[3.3.1.0²,⁴]nonanebromide

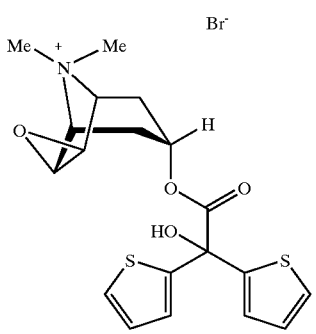

We claim:
1. A process for preparing a compound of formula 1

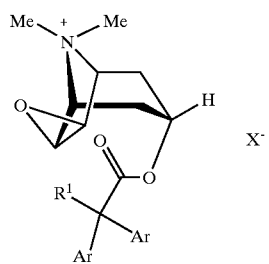

1 from a compound of formula 2

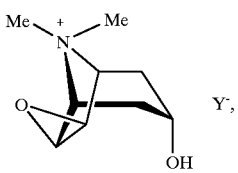

2 the process comprising reacting in one step the compound of formula 2 with a compound of formula 3

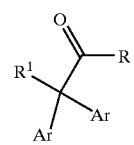

3 wherein:
X⁻ is chlorine, bromine, iodine, methanesulfonate, or trifluoromethanesulfonate;

$R^1$ is hydroxy, $C_1$–$C_4$-alkyl, $C_1$–$C_4$-alkoxy, $CF_3$, or fluorine;

Ar is phenyl, naphthyl, thienyl, and furyl, each optionally mono- or disubstituted with one or two groups selected from $C_1$–$C_4$-alkyl, $C_1$–$C_4$-alkoxy, hydroxy, fluorine, chlorine, bromine, or $CF_3$;

$Y^-$ is chlorine, bromine, iodine, methanesulfonate, or trifluoromethanesulfonate; and R is hydroxy, methoxy, ethoxy, O—N-succinimide, O—N-phthalimide, phenyloxy, nitrophenyloxy, fluorophenyloxy, pentafluorophenyloxy, vinyloxy, 2-allyloxy, —S-methyl, —S-ethyl, or —S-phenyl.

2. The process according to claim 1, wherein:

$X^-$ is bromine, methanesulfonate, or trifluoromethanesulfonate;

$R^1$ is hydroxy, methyl, $CF_3$, or fluorine;

Ar is phenyl, thienyl, or furyl;

$Y^-$ is bromine, methanesulfonate, or trifluoromethanesulfonate; and

R is hydroxy, O—N-succinimide, O—N-phthalimide, vinyloxy, or 2-allyloxy.

3. The process according to claim 1, wherein:

$X^-$ is bromine, methanesulfonate, or trifluoromethanesulfonate;

$R^1$ is hydroxy or methyl;

Ar is phenyl or thienyl;

$Y^-$ is bromine, methanesulfonate, or trifluoromethanesulfonate; and

R is hydroxy, O—N-succinimide, O—N-phthalimide, vinyloxy, or 2-allyloxy.

4. The process according to claim 3, wherein R is vinyloxy or 2-allyloxy.

5. The process according to claim 1, wherein the reaction is carried out in an organic solvent selected from acetonitrile, nitromethane, formamide, dimethylformamide, N-methylpyrrolidinone, dimethylsulfoxide, or dimethylacetamide.

6. The process according to claim 2, wherein the reaction is carried out in an organic solvent selected from acetonitrile, nitromethane, formamide, dimethylformamide, N-methylpyrrolidinone, dimethylsulfoxide, or dimethylacetamide.

7. The process according to claim 3, wherein the reaction is carried out in an organic solvent selected from acetonitrile, nitromethane, formamide, dimethylformamide, N-methylpyrrolidinone, dimethylsulfoxide, or dimethylacetamide.

8. The process according to claim 4, wherein the reaction is carried out in an organic solvent selected from acetonitrile, nitromethane, formamide, dimethylformamide, N-methylpyrrolidinone, dimethylsulfoxide, or dimethylacetamide.

9. The process according to claim 1, wherein R is hydroxy and activating reagents selected from carbonyldiimidazole, carbonyldi-1,2,4-triazole, dicyclohexylcarbodiimide, and ethyldimethylaminopropylcarbodiimide are used.

10. The process according to claim 2, wherein R is hydroxy and activating reagents selected from carbonyldiimidazole, carbonyldi-1,2,4-triazole, dicyclohexylcarbodiimide, and ethyldimethylaminopropylcarbodiimide are used.

11. The process according to claim 3, wherein R is hydroxy and activating reagents selected from carbonyldiimidazole, carbonyldi-1,2,4-triazole, dicyclohexyl carbodiimide, and ethyldimethylaminopropylcarbodiimide are used.

12. The process according to claim 4, wherein R is hydroxy and activating reagents selected from carbonyldiimidazole, carbonyldi-1,2,4-triazole, dicyclohexyl carbodiimide, and ethyldimethylaminopropylcarbodiimide are used.

13. The process according to claim 1, wherein the reaction is carried out at a temperature below 30° C.

14. The process according to claim 1, wherein the reaction is carried out at a temperature between −20° C. and 20° C.

15. The process according to claim 2, wherein the reaction is carried out at a temperature between −20° C. and 20° C.

16. The process according to claim 3, wherein the reaction is carried out at a temperature between −20° C. and 20° C.

17. The process according to claim 4, wherein the reaction is carried out at a temperature between −20° C. and 20° C.

18. The process according to claim 1, wherein the reaction is carried out in the presence of an organic or inorganic base.

19. The process according to claim 2, wherein the reaction is carried out in the presence of an organic or inorganic base.

20. The process according to claim 3, wherein the reaction is carried out in the presence of an organic or inorganic base.

21. The process according to claim 4, wherein the reaction is carried out in the presence of an organic or inorganic base.

22. The process according to claim 1, wherein $R^1$ is hydroxy and the reaction is carried out in the presence of zeolites as catalyst.

23. The process according to claim 2, wherein $R^1$ is hydroxy and the reaction is carried out in the presence of zeolites as catalyst.

24. The process according to claim 3, wherein $R^1$ is hydroxy and the reaction is carried out in the presence of zeolites as catalyst.

25. The process according to claim 4, wherein $R^1$ is hydroxy and the reaction is carried out in the presence of zeolites as catalyst.

* * * * *